US006444437B1

(12) United States Patent
Sporleder et al.

(10) Patent No.: US 6,444,437 B1
(45) Date of Patent: Sep. 3, 2002

(54) PROCESS FOR THE PRODUCTION OF NUTRITIONAL PRODUCTS WITH MICROORGANISMS USING SEQUENTIAL SOLID SUBSTRATE AND LIQUID FERMENTATION

(75) Inventors: Robert A. Sporleder, Berthoud; James C. Linden, Loveland; Herbert A. Schroeder; Donald Johnson, both of Fort Collins; Linda L. Henk, LaPorte; Robert P. Tengerdy, Fort Collins, all of CO (US); George Szakács, Budapest (HU)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/357,337

(22) Filed: Jul. 14, 1999

Related U.S. Application Data
(60) Provisional application No. 60/092,747, filed on Jul. 14, 1998.

(51) Int. Cl.⁷ .......................... C12P 39/00; A01N 63/00
(52) U.S. Cl. .................... 435/42; 435/209; 435/195; 435/201; 426/54; 424/93.1; 424/93.3
(58) Field of Search ................... 435/41, 42, 804, 435/209, 71.2, 195, 197, 201; 426/54; 424/93.1, 93.3

(56) References Cited

U.S. PATENT DOCUMENTS

| | | | | |
|---|---|---|---|---|
| 3,398,055 A | * | 8/1968 | Bruno | 435/71.2 |
| 3,937,845 A | * | 2/1976 | Han et al. | 426/53 |
| 3,990,945 A | * | 11/1976 | Huff et al. | 195/33 |
| 4,447,530 A | * | 5/1984 | Young | 435/68 |
| 4,952,505 A | * | 8/1990 | Cho | 435/209 |
| 5,047,332 A | * | 9/1991 | Chahal | 435/42 |
| 5,733,758 A | * | 3/1998 | Nguyen | 435/162 |

OTHER PUBLICATIONS

Oh et al., in Kon O. L., et al. (Ed.). ICSU Short Reports, vol. 6. Contemporary Themes in Biochemistry; 1986, pp. 514–516, Cambridge University Press.*
Sim, et al., Microb. Util. Renewable Resour. (1989), 6, 220–7.*
Coronel, et al., Philippine J. Sci. (1991), 120(3), 283–303.*
Bartholomew, W.H. et al. "Economics of Fermentation Processes" (1979) *Microbial Technology* 2:463–496.*
Beldman, G. et al.,"The Cellulase of *Trichoderma viride*. Purification, Characterization and Comparison of all Detecable Endoglucanases, Exoglucanases and β–Glucosidases" (1985) *Eur. J. Biochem.* 146:301.*
Desgranges, C. et al. "Effect of pCO₂ on growth, conidiation, and enzyme production in solid–state culture on *Aspergillus niger* and *Trichoderma viride* TS" (1990) 12:546–551.*

Henk, L.L. et al., "Solid–State Production of Ethanol from Sorghum" (1996) *Appliced Biochemistry and Biotechnology* 57:489–501.*
Henk, L.L. et al., "Simultaneous ensiling and enzymatic hydrolysis of structural polysaccharides" (1992) *Enzyme Microb. Technol.* 14:923–930.*
Hurst, P. L. et al., "Substrate Specificity and Mode of Action of a Cellulase from *Aspergillus niger*" (1978) *Biochem. J.* 169:389–395.*
Klappach, et al., "Manufacture of microbial biomass by solid phase fermentation with fungi" (1988) Ger. (East) DD 256,332, *Chem.Abstr.* 110:25, Jun 19, 1989, Abstract No. 230201k.
Klysosov, A., "Trends in Biochemistry and Enzymology of Cellulose Degradation" (1990) *Biochem. USA.* 29:10577.
Maloralla, B.L. et al., "Economic Evaluation of Alternative Ethanol Fermentation Processes" (1984) *Biotechnology and Bioengineering* 26:1003–1025.
Nandakumar, M.P. et al., "Mechanism of Solid Particle Degradation by *Aspergillus niger* in Solid State Fermentation" (1994) 29:545–551.
Puniya, A.K. et al., "Single cell protein: A promising dietary substitute" (1995) *Indian Journal of Experimental Biology* 33:545–551.
Peppler, H.J., "Production of Yeasts and Yeast Products" (1979) *Microbial Technolgy* 51:157–185.
Rivera–Munoz, G. et al., "Pruduction of Microbial Lapases in a Solid State Fermentation System" (1991) *Biotechnology Letters* 13(4):277–280.
von Sivers, M. et al., "A Techno–Economical Comparison of Three Processes for the Production of Ethanol from Pine" (1995) *Bioresource Technology* 51:43–52.
Whitaker, D. Cellulases, in *The Enzymes, V.* (Boyer, P., ed.), Academic Press, NY, 273 (1971).

* cited by examiner

*Primary Examiner*—Irene Marx
(74) *Attorney, Agent, or Firm*—Greenlee, Winner and Sullivan, P.C.

(57) ABSTRACT

Rural biomass and other cellulosic materials are converted to a protein-enriched animal feed supplement or to single-cell protein by a series of bio-reactions. A first stage bio-reaction is a solid substrate bio-reaction. Enzymes, such as cellulase, produced by the first-stage bio-reaction are added to a second-stage bio-reaction. Raw second-stage bio-reaction feedstock is pretreated to hydrolyze hemicellulose and/or to partially digest starch in the feedstock. In the second-stage bio-reaction, the feedstock is substantially digested and single-cell protein is harvested in an aerobic bio-reaction, while ethanol is produced in an anaerobic reaction. Products of the invention can serve as feed supplements to enhance protein content of animal feed.

8 Claims, 8 Drawing Sheets

PROCESS FOR THE PRODUCTION OF NUTRITIONAL PRODUCTS WITH MICROORGANISMS USING SEQUENTIAL SOLID SUBSTRATE AND LIQUID FERMENTATION

CROSS REFERENCE TO RELATED PATENT APPLICATIONS

This application is related to and claims priority from Provisional Patent Application No. 60/092,747, filed Jul. 14, 1998, titled "Fermentation Process Utilizing Various Substrates," the contents of which are incorporated herein by reference.

BACKGROUND OF THE INVENTION

This invention relates to a multiple-stage bio-reaction process.

Bio-reactions, including fermentation, are used for the production of many useful and valuable commercial products, including the production of ethanol or single cell protein. The commercial viability of a large-scale bio-reaction often depends, however, on the organic materials used as starting material or feedstock for the process. If the materials are expensive, such as corn or corn by-products, the profits of the bio-reaction process can be small. The availability of the materials for a feedstock can be uncertain since other potential uses for the materials can affect market price and availability. It has long been a goal to find a process to use low-quality biomass, which tends to be inexpensive and in large supply, as a feedstock for large scale bio-reaction. Such materials tend to be either agricultural wastes or waste products from industrial processes (such as from the food industry). It has also long been a goal to find a process that will fully utilize high-cost, high-quality feedstock materials such as corn. Most current bio-reaction processes utilize only a portion of the readily available carbohydrates, such as starch, and are unable to fully utilize those that are bound as part of the lignocellulose in the form of hemicellulose and cellulose. Because of this, conventional bio-reaction processes can only utilize approximately 60% of the total nutrients in cereal grains such as corn.

The success of a bio-reaction method capable of utilizing inexpensive feedstocks could have large consequences for many important industrial markets, including those for meat production (i.e. the use of bio-reaction products such as single cell protein as animal feed) and for energy (e.g. the production of ethanol as a fuel additive). Conventional methods, however, are inefficient because they involve complex and costly methods for pre-treating the raw feedstock materials, require costly commercially available purified concentrated enzymes, or poorly utilize the feedstock in the bio-reaction process.

A significant practical impediment to the use of various bio-reaction feedstock materials is the need to purify degradative enzymes such as amylases and cellulases used in the pre-treatment of the raw feedstock. Because these enzymes are themselves produced by microbes in an enzyme-production bio-reaction, the volume in which the enzymes are produced is generally large, requiring significant concentration of the enzymes. Furthermore, in order to aid in the recovery of the enzymes, it is often easier to use liquid bio-reaction which, unlike solid-substrate bio-reactions, does not leave solid residuals which would impede the recovery and concentration of the produced enzymes. For enzyme production the prior art has avoided using solid-substrate bio-reactions because of difficulty of purifying enzyme products, even though the same microbes grow better in a solid-substrate bio-reaction.

It should also be noted that the use of certain raw feedstock materials requires acid hydrolysis pre-treatment in order to render the material accessible to degradatory enzymes during the bio-reaction process. For example, before feedstocks with high cellulosic content can be successfully treated with cellulase enzyme complex, the hemicelluloses are acid hydrolyzed to release the cellulose from lignin, and thus open the cellulosic structure to action by the cellulase enzyme complex. The acid is subsequently neutralized prior to bio-reaction.

Because of its low cost, sulfuric acid is typically used for pre-treatment hydrolysis. However, residual high sulfate content subsequent to neutralization inhibits the subsequent bio-reaction. Furthermore, because of its low cost, slaked lime ($Ca(OH)_2$) is often used as the neutralizing agent. The resultant $CaSO_4$ salt precipitates from the pretreatment suspension, and is removed prior to the bulk bio-reaction as a waste product. The need to remove this precipitate adds cost and complexity to the process, without directly improving the product. It would be advantageous to use a method of acid hydrolysis and neutralization that provides acceptable costs, low or zero waste emission, and directly contributes to the value of the resultant bio-reaction product.

The methods of the present invention can be used to overcome the deficiencies of the prior art, and are described herein.

SUMMARY OF THE INVENTION

The present invention uses enzymes produced by a first stage bio-reaction without an intermediate step of enzyme purification. These enzymes can be used directly in a second stage bio-reaction to make high effective use of the feedstock. By so doing, the costs and inefficiencies of enzyme concentration and purification are avoided. Furthermore, the benefits of solid substrate bio-reaction for the production of enzymes can be obtained, without the disadvantages that a solid substrate bio-reaction poses in enzyme purification.

The production of animal feed single-cell protein product from bio-reaction feedstocks with high cellulosic content requires acid hydrolysis followed by base neutralization. It is also a teaching of the present invention that acids and bases be used that have value as nutritional supplements. Thus, given that phosphate minerals are often added as a nutritional supplements in cattle feed, and are also beneficial to microbial growth in the second stage bio-reaction, it is advantageous to use phosphoric acid for acid hydrolysis pretreatment of the raw second stage bio-reaction feedstock, so that its continued presence benefits the second stage bio-reaction, and furthermore adds nutritional value to the animal feed product.

Likewise, the use of ammonium ion (e.g. as ammonium hydroxide or anhydrous ammonia) is beneficial to neutralize the phosphate used in the acid hydrolysis since ammonia provides nutritional value both to the microbes used in the second stage bio-reaction, as well as in the final animal feed product, the ammonia serving as non-protein nitrogen supplement.

The benefits and advantages of the present invention will become more apparent in the specification provided below.

DETAILED DESCRIPTION OF THE INVENTION

The Koji process has been used in the production of the alcoholic beverage sake for two millennia. The process begins with a solid-feedstock fermentation of rice by *Aspergillis oryzae*, in which amylase enzyme is produced by the microbe due in part to stimulation by the large amount of starch present in the rice. The fermented solid state feedstock is subsequently incubated with additional rice and a second microbe in an aqueous fermentation, in which the amylase acts on the additional rice starch to make it available to the second microbe. While this process is still in general use in the Japanese brewing industry, the use of solid feedstock fermentation for the production of purified industrial enzymes is only rarely studied or practiced in modern times.

While the ancient Koji brewers were artful and path-breaking in their microbiology, their chemistry was less advanced. Thus, the rice feedstock that they used was quite available to the fermentation microbes, and required no special pre-treatment other than cleaning and steaming the rice. Furthermore, their process did not require complete utilization of the rice feedstock for a high quality sake product.

The present invention is directed towards the conversion of rural biomass, industrial byproducts and/or high quality cereal grains to high protein animal feed product, protein hydrozylates for human consumption, ethanol in combination with animal feed co-products, or other such commercially valuable products as produced by bio-reaction. More than one bio-reaction is used in the process—a first-stage bio-reaction performed generally as a solid substrate bio-reaction in order to produce enzymes, which are then used in a second-stage bio-reaction in order t o produce the desired product.

Some amount of chemical and/or physical pre-treatment of the raw feedstock materials for one or both of the first and second stage bio-reactions may be necessary in order to make the desired feedstock materials available to the bio-reaction microbes. Various characteristics of the bio-reactions, including but not limited to the feedstock materials, the microbes, the pre- and post-treatments of the feedstock materials, and the like, can be modified to optimize different parts of the process, in order to optimize the over-all yield of desired end-products such as single-cell protein for animal feed.

Figure 1:
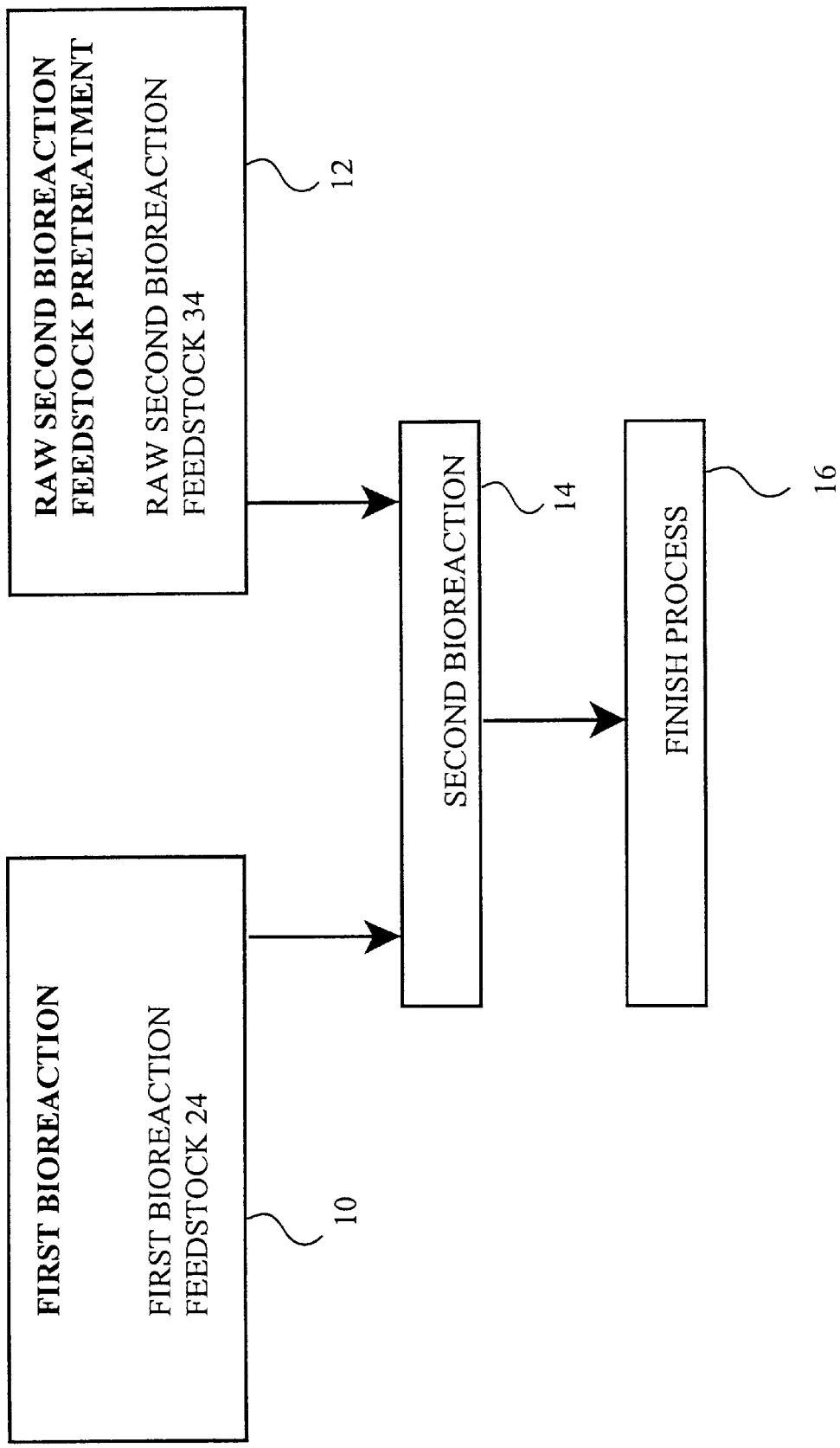
FIG. 1 is a simplified flow diagram of two linked bio-reactions.

FIG. 1 is a simplified flow diagram of the methods of the present invention. In a first-stage bio-reaction 10, a first-stage feedstock 24 is used for the production of enzymes, which can be used to hydrolyze a raw second-stage bio-reaction feedstock 34. In general, the amount of the first-stage feedstock 24 is small in comparison with the amount of the second-stage feedstock 48, as will be described below.

In a second-stage feedstock pretreatment step 12, the raw second stage feedstock 34 is pre-treated so as to render it more fully accessible to enzymatic hydrolysis by the products 60 arising from the first bio-reaction 10. In a second-stage bio-reaction 14, both first bio-reaction products 60 and pretreated second-stage feedstock 48 are combined, and other ingredients added so as to initiate the second-stage bio-reaction, the end result of which will be a product containing high levels of single cell protein, ethanol, or other direct bio-reaction product. In a final step 16, the bio-reaction products are further processed in order to create commercially saleable or useful products. For example, if a single cell protein is produced, the single cell protein can be further processed in a liquid blending facility that will produce a variety of specific liquid feed products, dehydrated to form a solid protein source, or otherwise treated to make a feed product. If ethanol is produced, it can be separated, concentrated or purified by conventional means appropriate to the end use of the ethanol, and the bio-reaction by-product including single-cell protein can be further processed to make a feed product.

Appropriate feedstocks for the present invention include but are not limited to cereal grains such as corn, milo, wheat, rice, and millet, forage crops such as sweet sorghum, high yield grasses such as switchgrass and *Sericea lespediza*, agricultural byproducts or residues such as corn husks, corn stover, milo stubble, soybean residue, sugar beet residue, sugar cane bagasse, and grain cleanings, cereal straws such as wheat straw, industrial byproducts such as spent brewer's grain, spent brewer's products and wastes, distillery grain, corn wet milling byproducts, wheat milling byproducts, dairy byproducts, paper byproducts, and candy byproducts, forestry byproducts such as wood chips, saw dust, pulp byproducts, industrial wastes such as waste activated sludge, meat processing wastes, paper wastes, or certain chemical industry wastes. Any other feedstock material that contains protein, carbohydrate or lipid nutrients is appropriate for this process.

Agricultural residues are of particular interest, since they are produced in such copious quantities, estimated at 400 million tons a year in the United States. These products are comprised primarily of cellulosic materials, and compositional analysis of agricultural residues such as sugarcane bagasse, wheat straw, rice straw and corn stover yield 30–37% cellulose and 16–30% hemicellulose, both of which can serve as sources of bio-reaction feedstock in the present invention.

It should be noted that the first stage bio-reaction feedstock 24 and the raw second-stage feedstock 34 can be comprised of the same basic materials, such as from the above list, or can be distinct from one another. For example, spent brewers grain (SBG) can be used as the feedstock 24 in the first-stage bio-reaction 10, and wood chips can be used as the raw feedstock 34 in the step 12 pre-treatment, or visa versa. Furthermore, more than one different feedstock material, such as spent brewer's grain and pulp byproducts, can be mixed together to create the first bio-reaction feedstock 24 or the raw second-stage feedstock 34. The suitability of various feedstock materials for either the first-stage feedstock 24 or for the raw second-stage feedstock 34 will be discussed in more detail in a later section.

This process utilizes many feedstock materials. Indeed, in a number of cases, companies must pay contractors to haul away the feedstock materials and nutriments suitable for the invention since they are considered of little or no value, and are thereafter often disposed in landfill or create an environmental problem. The process of the invention can make use of otherwise low-value or useless material as feedstocks for the bio-reaction of valuable products. Thus, the methods of the present invention are not only economically profitable, but also alleviate significant environmental waste problems.

First-stage Bio-reaction

Figure 2:
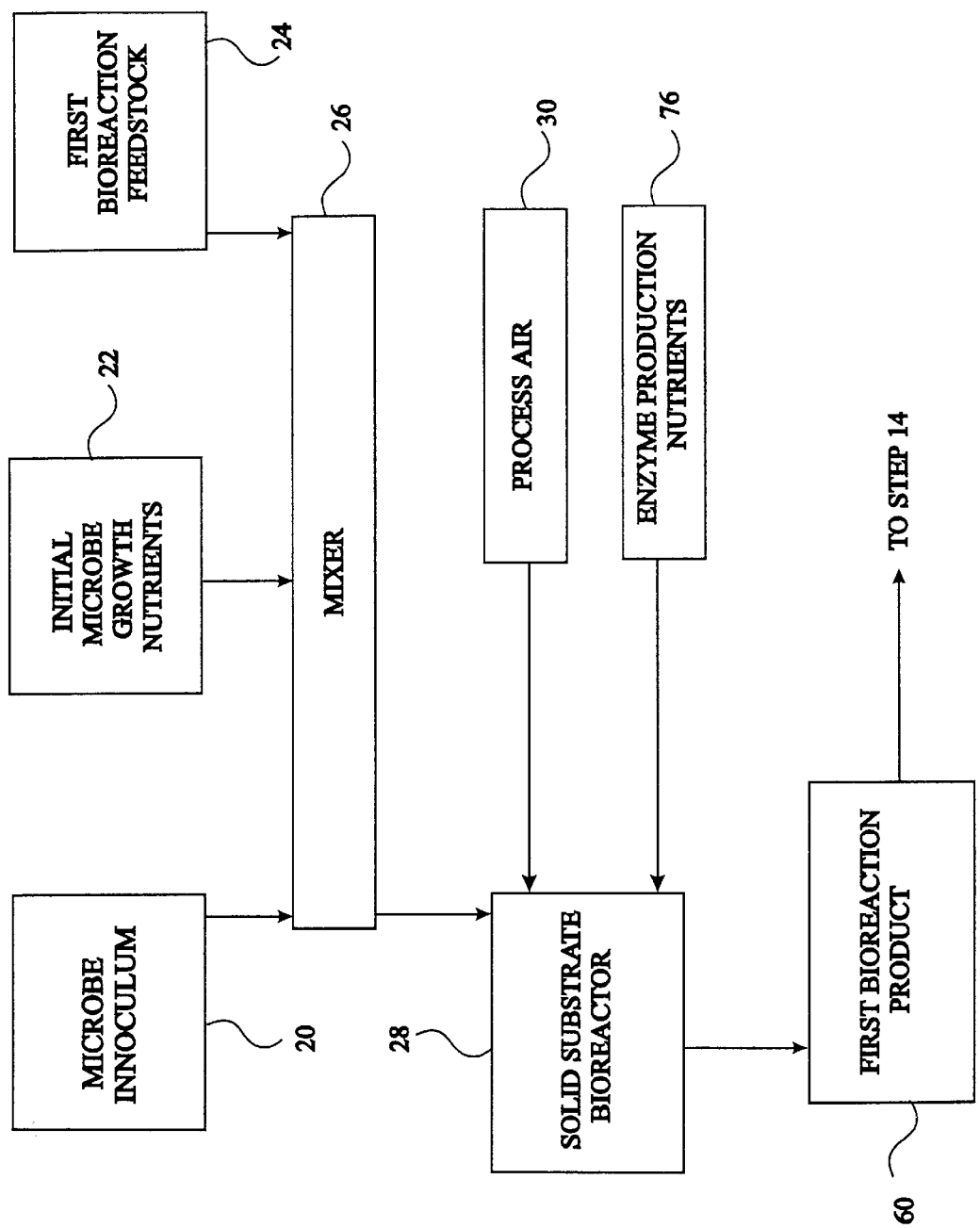
FIG. 2 is a flow diagram of the first stage bio-reaction process 10.

FIG. 2 is a flow diagram of the first stage bio-reaction 10. Many different enzymes can and will be produced depending upon the inputs to the process of FIG. 2, which are chosen with regard to market availability and compatibility with the raw second-stage bio-reaction feedstock 34 chosen for the pre-treatment of step 12 and the second-stage bio-reaction of step 14. Enzymes produced during the first-stage bio-reaction include but are not limited to amylases and amyloglucosidases for the hydrolysis of gelatinized starches from cereal grains, cellulase complexes, pectinases, xylanases and β-glucosidases for the hydrolysis of cellulosic materials such as those found in corn husks, proteases for the hydrolysis of proteins and lipases for the hydrolysis of lipids such as those found in meat processing wastes, ligninases for lignin degradation, and phytases and glucanases β-glucanases for the processing of nutrients for use in poultry feed.

An enzyme-enhanced product 60 is the end result of the first-stage bio-reaction in FIG. 2. The enzyme-enhanced product 60 is, in and of itself, of commercial value, as will be described later. For example, the product 60 can be added to a feed ration to allow an animal to more fully utilize other dietary components, or it can serve as an input for the production of purified or enriched hydrolytic enzymes for other processes.

First-stage bio-reaction takes place in a solid substrate bio-reactor 28. A solid substrate bio-reaction is designed for optimum growth of microorganisms on surfaces, particularly the surface of solid or solid substrate feedstock materials. Microorganisms useful in the first stage bio-reaction, such as *Trichoderma reesei*, grow preferably on surfaces of feedstock and can be stimulated to produce enzymes useful in biomass degradation, such as cellulases, when grown on a cellulosic surface. In conventional bio-reactions, microbial cells are grown as a suspension in liquid media. In a solid substrate bio-reaction, microbial cells grow while attached or resting on feedstock surfaces. The feedstock has appreciable. Moisture content but not appreciable free liquid. The solid substrate bio-reactor 28 can be of varied size and shape dependent upon the volume of feedstock 24 to be processed, and the type of enzyme to be produced. A general configuration for a solid substrate bio-reactor 28 that will allow most feedstock materials to be used and will also allow most enzymes to be produced is a cylindrical, spherical, or rectangular parallelepiped constructed of stainless steel or other corrosion-resistant material. Other suitable materials include, but are not limited to, plastic, fiberglass and non-stainless steel. The bio-reactor 28 is designed to allow the feedstock 24 to reside on one or more horizontal partitions suspended above the floor of the bio-reactor 28, wherein the partition can be perforated to allow sterile air permeation as described below. The solid substrate bio-reactor 28 is designed to allow an airflow to permeate the feedstock 24, allow the temperature to be controlled, and allow the contents to be humidified. These parameters can function in concert; for example, humidified air not only maintains the moisture of the solid feedstock, but also cools the bed as evaporation removes heat that is produced by microbial metabolism in the solid mass of feedstock 24. The temperature, humidity and airflow within the bio-reactor 28 are the primary process parameters generally needed for the solid substrate bio-reaction. Depending on the process inputs to be described later, it can also be useful for the bio-reactor 28 to include provisions for the mechanical agitation of the feedstock 24, while maintaining sterility, for the addition of nutrients during the bio-reaction, or for pressurization of the bio-reactor 28. The uses of these capabilities will be described below. Notwithstanding the many design choices provided above, a conventional Koji chamber, used in the production of sake, can be employed for the first stage bio-reaction.

The water-content of the feedstock can vary according to the feedstock material. Solid substrate bio-reaction is meant to lack substantial free liquid, which would pool or drain from the feedstock surfaces, taking with it some of the produced enzymes. Thus, with a non-porous, relatively hydrophobic feedstock, the water-content of the bio-reaction would be relatively low, whereas with porous or hydrophilic feedstock materials, the water-content of a solid substrate bio-reaction will be higher. Most often, the dry matter of a solid substrate bio-reaction will be less than 40%. Using spent brewer's grain as the first bio-reaction feedstock, for example, water content of 66% is near optimal. Despite the high moisture content, liquid water is preferably not present in a solid substrate bio-reaction.

It should be noted that some of the degradative enzymes mentioned above represent not a single protein, but families of proteins with similar functionality, which are for purposes of this description called complexes. For example, *T. reesei* produces at least a dozen distinct cellulase enzymes, and *Clostridium thermocellum* produces at least 15 such enzymes. In addition, the enzymes are often found in conjunction with enzymes such as γ-glucosidases which act on cellulose breakdown products.

The first-stage bio-reaction begins when sterilized feedstock 24 is mixed with a microbe inoculum 20 and initial microbe growth nutrients 22 in a mixer 26. All bio-reactions are carried out under sterile conditions to prevent the introduction and growth of undesired organisms. The choice of the specific microbe inoculum 20 is dependent upon the specific feedstock selected for the first bio-reaction 24 enzyme-production step 10, the specific raw second-stage bio-reaction feedstock, 34, of the pretreatment step 12 that is selected, as well as the desired final product. For example, for the production of cellulase complexes on cellulose-rich food processing waste, such as spent brewer's grain, the inoculum 20 can conveniently include *Trichoderma reesei* Rut-C30 (ATCC #56765) Rhizopus oryzae or other microbes that are suitable for cellulase production, which include *T. hamatum* and Gliocladium Tub F-105. For the production of amylase enzymes on a starch-enriched feedstock such as corn wet-milling byproducts, the inoculum 20 can include a strain of *Aspergillis oryzae, A. niger, Rhizopus oligosporus*, or *Rhizopus oryzae*. *Phanerochaete chrysoporium* is a known source of ligninase for use with high lignin-content biomass conversion. It should be noted that most of the microbes above produce many different hydrolytic enzymes. For example, the microbe *Rhizopus oligosporus* produces a variety of enzymes, including cellulase, amylase, xylanase, β-glucosidase, and amyloglucosidase, which separately and in combination have beneficial hydrolytic activity on a large variety of feedstock materials. Various strains of the described organisms have been selected for enhanced ability to produce various enzymes. The preferred strain chosen will depend upon specific enzymes whose production is desired, growth characteristics, and other factors known to those skilled in the art. Specific initial microbe growth nutrients 22 are dependent upon the microbe inoculum 20, the specific enzyme chosen for production and the desired rate of microbial growth and enzyme production, which is dependent upon overall process timing needs, and the composition of the feedstock 24.

First-stage bio-reaction 10 can be considered to take place in two separate phases, although the two phases have substantial overlap. In the first phase of microbe growth, the initial microbial mass of the inoculum 20 is increased. In fact, the inoculum 20 can consist primarily of spores or of other microbes in a relatively inert biological state, which are then cultivated in a seed inoculum train and then added to the bio-reactor 28 that creates a rapidly growing microbial mass. During this phase, the focus is on increasing microbial mass, which is required for the production of large quantities of enzymes. After a sufficient microbial mass is achieved, however, it is desirable in a second phase for the microbial mass to divert a significant fraction of its biological output from growth of microbial mass to enzyme production. Furthermore, to increase enzyme production in this second phase, it is frequently effective to expose the microbes to additional nutrient sources, which stimulate the production of the enzymes needed to convert unavailable nutrients to usable food sources. For example, for the production of cellulase complex, it is advantageous during the second phase of enzyme production, to provide a primary food source for the microbes containing a high cellulose content, thereby encouraging the production of cellulase. The supplemental nutrient solution added to stimulate the production of enzymes should contain the minerals, vitamins, nitrogen and additional energy sources that are the limiting factors for optimum enzyme production.

In the following discussion, the processes of the present invention are described as if relating to the production of cellulase-complex for the bio-reaction of second-stage feedstock materials with high cellulosic content. It should be understood, however, that the same processes are also applicable to other bio-reactions that require or benefit from the production of enzymes other than cellulase complexes used in the utilization of cellulosic materials.

It can be seen that the first stage bio-reaction feedstock materials can be chosen that will provide a proper mix of nutrients for the different phases of enzyme production. For example, the use of spent brewers grain (SBG) from certain sources yields very high levels of cellulase complex when $T.$ $reesei$ is used as the feedstock 24, even with the use of minimal growth nutrients 22. The primary source of SBG is from beer breweries, and certain breweries steep the grain under conditions that extract more of the available food source from the grain, while others treat the grain under less harsh conditions. In general, it is considered that some amount of available starch remain in order to support the initial microbial mass growth. Other factors contributing to differences in cellulase-complex yields can include the source of the brewer's grain, as different breweries use different blends of grains and other ingredients from different sources.

The initial microbe growth nutrients 22 are formulated to supplement the intrinsic nutrients of the feedstock 24, so as to provide increase in microbial mass in the first phase of the bio-reaction. When sufficient mass of microbes is attained, the bio-reaction step 10 is supplemented with enzyme production nutrients 76, which are chosen to stimulate enzyme production. For example, in the case of cellulase-complex production, depending on the microbe inoculum 20, the feedstock 24, and other process parameters, the enzyme production nutrients 76 can include nitrogen-containing compounds (e.g. ammonium nitrate, ammonium sulfate or ammonium chloride) required for protein production. In addition, cellulosic material in the form present in the raw second-stage feedstock 34 can also be introduced, in order to encourage the composition of cellulase-complex most effective at hydrolyzing the cellulose present within the second-stage feedstock.

The enzyme production nutrients 76 improve the production of enzymes using $Rhizopus\ oryzae$ on spent brewers grain (SBG). Parallel first stage bio-reactions were carried out using either tap water or nutrients 76 in mixtures of 5 g SBG to 10 ml of solution. The nutrients 76 used were 5 g/L $NH_4NO_3$, 5 g/L $KH_2PO_4$, 1 g/L $MgSO_4 \times 7H_2O$, 1 g/L NaCl, and trace elements adjusted to a pH of 6.0. After 1 day of solid substrate bio-reaction, the following approximate enzyme quantities were produced by the two bio-reactions, all expressed in terms of enzyme per gram dry weight SBG.

|  | With nutrients 76 | Without nutrients |
| --- | --- | --- |
| Alpha-amylase (IU) | 140 | 43 |
| Amyloglucosidase (IU) | 65 | 28 |
| Xylanase (IU) | 13 | 4 |
| Cellulase (FPU) | 0.65 | 0.65 |
| Beta-glucosidase (IU) | 9 | 1 |
| Endoglucanase (EGU) | 380 | 240 |

Other than cellulase, levels of enzymes in the nutrient 76 fed bio-reactions reached peak values after a single day of incubation, whereas with tap water, enzyme levels peaked after 3 to 6 days.

It should be appreciated that for the use of many cellulose-containing feedstock materials 34, the amount and activity of the cellulase-complex formed in the step 10 bio-reaction will be a primary factor in the effectiveness of later steps. Thus, considerable care is taken to maximize enzyme yield in the first-stage bio-reaction 10. Particular attention must be given such that the nutrients, temperature, humidity and aeration are not limiting for enzyme production in the solid substrate bio-reaction. For example, care must be taken to permit significant air porosity in the feedstock 24. If the feedstock 24 has a high a water content (e.g. SBG), the feedstock material can collapse and provide insufficient aeration. This result can be countered by adding dry matter to the feedstock material to improve its ability to provide structural porosity. The added dry matter can conveniently be of the type to be used as the second-stage feedstock 34, so as to encourage the production of cellulase complex that effectively hydrolyzes this feedstock material. Alternatively, the feedstock 24 can be vigorously agitated with less than saturated air or drained in order to reduce the water-content of the feedstock 24, so as to provide initial air porosity. However, even with the supplementation with dry matter or the use of other methods to increase the initial air porosity, microbial growth will tend to take place preferentially in inter-particle gaps, resulting in increasingly less efficient aeration, particularly when the bed of solid feedstock is deeper than a 4–6 inches. Thus, as the first-stage bio-reaction progresses, aeration must be carefully controlled. For example, physical agitation of the solid substrate material will continually provide new routes for airflow, as is known in the art. However, the growth of some microbes can suffer from such handling, and in such cases, other means of increasing airflow and oxygenation of the feedstock mass can provide process air 30, which is controlled in temperature, humidity, flow rates, and potentially in pressure, as well. To improve oxygenation of the feedstock 24, oxygen-enriched streams can be introduced in the process air 30. In addition, large pressure differences (e.g. 2 or more atmospheres) can be generated across the solid feedstock to force air through.

The course of the bio-reaction can be monitored by temperature measurement, using one or more probes in the solid substrate material. The temperature rises during growth and metabolism of the microbes, then drops as metabolism shows and the bio-reaction nears completion. Enzyme yields are monitored by extracting a sample of bio-reaction material, then using standard assays known in the art for the enzymes of interest. Cellulase activity is measured in a standard filter paper test.

It should be appreciated that for efficient degradation of the raw second-stage feedstock 34 in the step 14, more than one enzyme can be effective. For example, cellulase-complexes from multiple microbial strains can attack different varieties of cellulose present within the raw second-stage feedstock 34, or the nutriment 34 can contain other food sources such as granular starch or lipids in addition to cellulose. In such cases, the microbe inoculum 20 can be comprised of more than one microbial strain or type, yielding a mixture of enzymes. Alternatively, enzyme products from multiple enzyme production processes, carried out in multiple bio-reactors 28, can be combined to form enzyme mixtures.

Bulk-Production Nutriment Pre-Treatment

Figure 3:
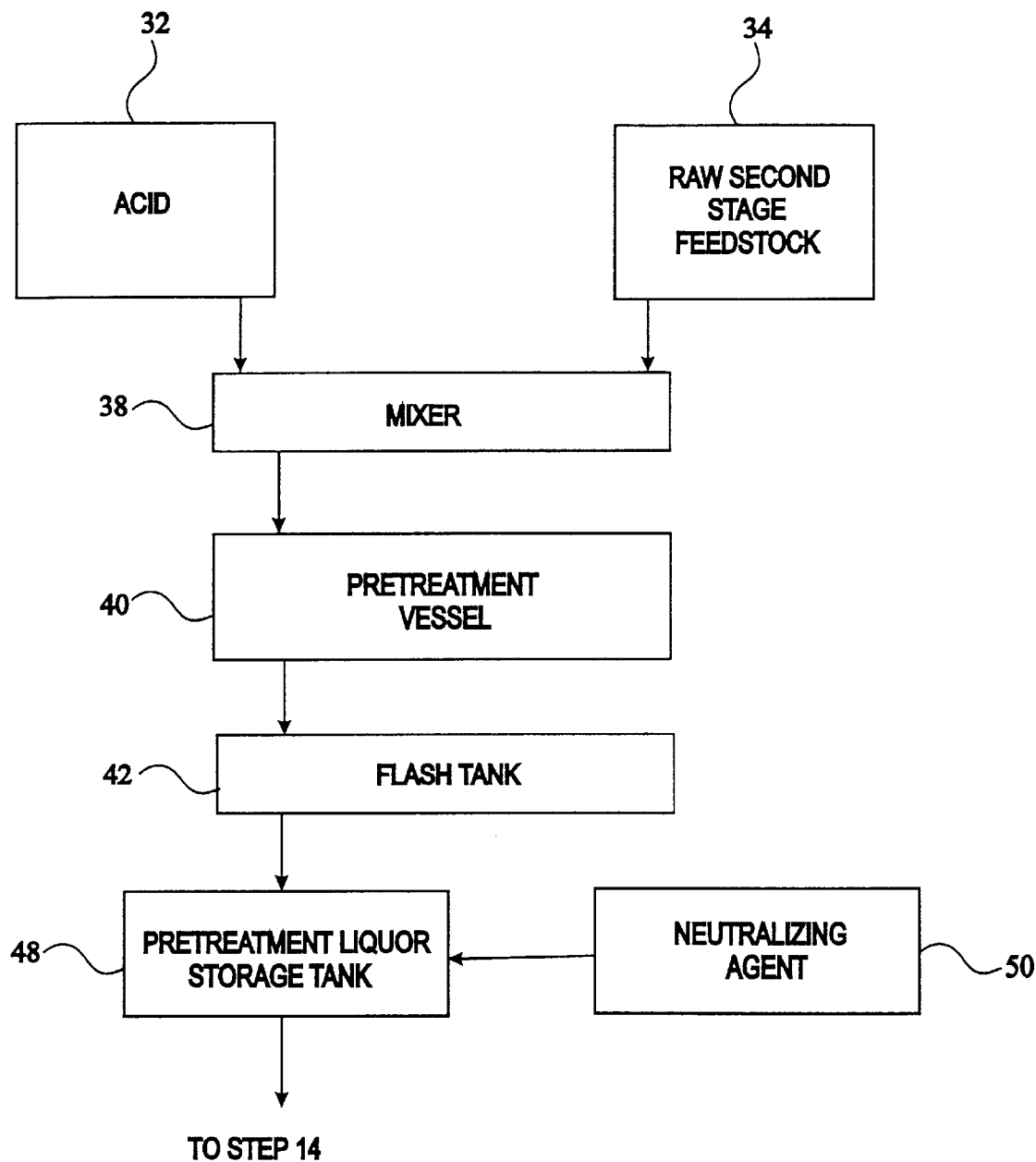
FIG. 3 is a flow diagram of the raw feedstock pre-treatment process 12.

FIG. 3 is a flow diagram of the raw second-stage feedstock pre-treatment process step 12. The purpose of the step 12 includes treating the raw second-stage feedstock 34 with acid to hydrolyze the hemicellulose, to remove lignin from the cellulose, which will allow the enzymes created in the first bio-reaction 10 to act upon the exposed cellulose in the second-stage bio-reaction step 14. Another purpose of the pre-treatment step 12 is to convert the hemicellulose to a fermentable sugar.

It is well-known to those skilled in the art that pre-treatment of cellulosic materials in acid conditions is effective in providing a good bio-reaction, and is often performed in conjunction with elevated temperatures and pressures. Typically, the acid used in the pre- treatment is sulfuric acid, due to its wide availability, low cost, and ease of disposal. In general, after the acid pre-treatment, the sulfuric acid is removed by neutralization with lime (calcium oxide) or slaked lime (calcium hydroxide) or some other mineral oxide that forms an insoluble precipitate (calcium sulfate in the case of lime). The precipitate is removed, and the materials subjected to conventional processing.

It should be noted that when a bio-reaction is directed to the production of single-cell protein for animal feed, the use of sulfuric acid is not economically optimal. In the present invention phosphoric acid has advantages in the overall process, since the phosphate from the pre-treatment can be used to improve the subsequent bio-reaction. Additionally, the phosphoric acid need not be removed from the pretreated feedstock 48 prior to bio-reaction, and when carried through the overall process into a single-cell protein based animal feed product, or in the co-fermentation by-product as in ethanol production, phosphate is an important animal feed supplement that must otherwise be provided to animals by other means.

Similar reasoning applies to the neutralizing agent used in the pre-treatment. To avoid forming an insoluble salt upon neutralization, ammonia (in gaseous or liquid forms) can be introduced to neutralize the phosphoric acid. The ammonium phosphate product is soluble, and the ammonium ion is useful for microbial growth in the subsequent second-stage bio-reaction, and further enriches the animal feed product of the overall process.

The following calculations demonstrate the cost of using phosphoric acid in the acid hydrolysis pre-treatment of SBG as the raw second-stage feedstock 34. The nutrient requirements for aerobic yeast growth can best be calculated from the composition of the yeast product. Yeast contains 2.6% (w/w) phosphorous, so that 4.1 g $H_3PO_4$/L is required for a bio-reaction with the goal of producing 50 g yeast/L. A pretreated SBG slurry of 0.22 kg dry matter/L concentration, which contains 496 g/kg of potentially bio-reactable sugars, will yield 50 g dry yeast/L, assuming 90% overall theoretical yield. These conditions yield a product that contains about 1.0% (w/w) phosphate. The process would require 17.0 kg $H_3PO_4$/ton dry matter which, with current prices of $280 per ton of phosphoric acid syrup, would cost $9.70/ton SBG dry matter. These calculations vary according to the acid concentration of the slurry, which in turn affects the time and temperature of pretreatment required to hydrolyze the SBG.

For example, SBG pre-treated with 0.5M phosphoric acid at 122° C. for 30 minutes yields over 250 mg of glucose per gram dry mass when treated with added cellulase, with similar glucose yields when using 1.0M phosphoric acid, instead. With switchgrass as the feedstock to be pretreated, a 10 minute treatment with 0.025M phosphoric acid at 190° C. also yielded over 250 mg of glucose per gram dry mass, while corn stover treated with 0.05M phosphoric acid at a temperature of 160° C. for 20 minutes yielded 360 mg glucose per gram of dry matter, both after incubation with cellulase enzyme. These results indicate that higher temperature incubation with lower phosphoric acid concentrations yields significant conversion of cellulosic material into cellulase accessible forms. Incubation temperatures over 122° C. are preferred in the nutriment pre-treatment process of the step 12.

Calculations for the entire process, including acid hydrolysis pretreatment, disposal of wastes, the need for additional nutritional supplementation, and the nutritional value of the final product are provided in the following table, in which corn stover is used as the raw second-stage feedstock 34, and all costs are figured per ton dry matter.

|  | 0.73% $H_2SO_4$ | 0.025 M $H_3PO_4$ | 0.01 M $H_3PO_4$ |
|---|---|---|---|
| Pre-treatment |  |  |  |
| Acid cost | $6.55 | $19.60 | $7.84 |
| Neutralization | $5.21 | $2.55 | $1.02 |
| Salt (e.g. $CaSO_4$ disposal) | 2.03 | $0.00 | $0.00 |
| Additional nutrients for bio-reaction | $3.62 | $0.00 | $0.00 |
| Total | $17.41 | $22.15 | $8.86 |
| Final % w/w $H_3PO_4$ in 50% syrup | 0 | 1.25% | 0.5% |

Overall, costs for the phosphoric acid treatment product is similar or significantly better than that for sulfuric acid pre-treatment product. In addition, the phosphoric acid pretreatment product, however, contains phosphate and ammonium in the final product at concentrations that are useful in animal feed, providing a strong benefit for use in animal feed production or as a co-product in ethanol production. It should be noted that other acids in addition to sulfuric acid and phosphoric acid can be used, including nitric, hydrochloric, lactic, formic, acetic and peracetic acids.

Peracetic acid is particularly effective in the treatment of woody cellulose materials, as demonstrated for example in the doctoral dissertation by Lincoln Teixeira for Colorado State University (1998). Peracetic acid in the range of 6–21% provides effective hydrolysis of cellulosic material, even when used at ambient temperature for 3–7 days. However, when 21% peracetic acid is used, which provides greatest accessibility of the cellulose content, subsequent bio-reaction of the pre-treated feedstock is less effective. The use of pre-treatment with 6–9% NaOH or higher prior to peracetic acid provides equivalent accessibility to the cellulose material even with peracetic acid concentrations in the range of 6–9%. However, because the peracetic acid and alkali-peracetic acid treatments results in the production of higher concentrations of xylans than do the dilute acidic hydrolyses, the use of xylanases in addition to cellulases results in better utilization of the cellulosic feedstock.

The feedstock pre-treatment step 12 begins when the raw second-stage feedstock 34 is placed in a mixer 38 along with a predetermined amount and dilution of an acid 32. Water can be added to make the final mixture 5–30% dry matter, and preferably 20–25% dry matter. After the mixer 38 combines the raw feedstock 34 and the acid 32, this mixture is then placed in the pre-treatment vessel reactor 40. While the pre-treatment can be carried out in a batch process, it is conveniently performed in a continuous process using a Sunds defibrator (Sunds, Norcoss, Ga.), a continuous pulp digester, extrusion screw or other continuous process vessel as the vessel 40. The time, temperature and heat of the process is highly dependent on the type and concentration of acid, and the composition of the raw feedstock. The range of temperatures range from 15° C. to 200° C., with pressures ranging from ambient pressure to 400 pounds per square inch. The time of treatment can be from 1 minute to as long as 60 days, although times of treatment in the range of 1 minute to 60 minutes are preferred for continuous flow treatment. In has been determined that for pretreatment of corn stover with aqueous phosphoric acid, concentrations in the range of 0.01 M to 0.2 M phosphoric acid yields good bio-reaction of the stover when treated for 10 to 60 minutes at temperatures between 160° C. to 190° C. It is also evident that longer pre-treatments at lower temperatures would provide adequate yields as well.

After completion of the pre-treatment process, the mixture is released to a flash tank 42. The release of the contents of the pretreatment vessel 40 to the flash tank 42 has some important considerations. The pretreatment vessel 40 frequently is under elevated heat and pressure that need to be dispersed. The contents of the pretreatment vessel 40 are introduced to the flash tank 42. Depressurization further ruptures particles of the pre-treated feedstock to allow a more complete bio-reaction and allows heat and pressure to be dispersed, through mixing with the cooler contents of the flash tank. Heat exchangers supplement the cooling process. In some instances the contents of the flash tank 42 will be agitated to further reduce heat and mix the contents.

Contents of the flash tank 42 are then transferred to a pretreated feedstock storage tank 48, and are neutralized by the addition of a neutralizing agent 50. As mentioned above, lime is the conventional neutralizing agent 50, creating an insoluble precipitate with sulfuric acid, the most common acid 32 used in acid hydrolysis. However, as also mentioned, it is preferred for the neutralizing agent to be ammonia (in either gaseous or aqueous form), which does not form an insoluble precipitate, and which can be a useful nutrient both for the second-stage bio-reaction and for the animal feed product of the overall process.

It should be noted that sterile or near sterile conditions are maintained throughout both the first-stage bio-reaction and the second-stage bio-reaction (below), as well as subsequent to the neutralization step of the second-stage feedstock pre-treatment, in order to prevent introducing contaminating microbes.

Second-stage Bio-reaction

In conventional bio-reactions using cellulosic feedstock materials, purified or semi-purified cellulase complex is frequently added to the cooled and neutralized second-stage feedstock 48. Conventionally, cellulase complex is generated from bio-reaction of cellulosic materials using high cellulase complex producing strains, such as $T.$ $reesei$. The yields of cellulase complex can be very low, since the complex can be bound to the bio-reaction feedstock, or because the extraction technique can be incomplete (especially in order to reduce the volume of extract from which the cellulase complex will be enriched or purified). Because degradation of cellulosic biomass is generally limited by the activity level of the cellulase complex in the reaction, low cellulase activity is a major deficiency in conventional processes. In addition to the incomplete yields of cellulase complex from the enzyme-production process of conventional processes, the purification or enrichment of the cellulase from the extraction fluids or the growth medium involves added expense to a process that may be of marginal economic profitability. Commercially enriched or purified cellulase complexes are generally quite expensive, and have made the use of biomass as a feedstock uneconomical.

In the present invention, however, the cellulase complex is not extracted, purified, enriched, or otherwise treated from the first-stage bio-reaction 10. Instead, the entire contents of the first-stage bio-reaction, including the first-stage product 60 and any initial growth nutrients 22 and added enzyme production nutrients 76, are added to the pre-treated, neutralized, and cooled second-stage bio-reaction feedstock 48. This direct combination of enzyme-enriched first stage bio-reaction products with the second-stage feedstock 48 has many benefits. For instance, all of the cellulase complex produced in the first bio-reaction 10 is added into the second bio-reaction, providing effectively 100% of the enzymes produced in step. 10. In general, this large yield of enzyme facilitates and accelerates the second-stage bio-reaction 14, since cellulase complex is often the limiting factor of such a process. Furthermore, the present invention eliminates the high costs associated with recovery and enrichment of cellulase complexes from the first-stage bio-reaction 10. Also, the first-stage feedstock 24 may not be fully exhausted during the bio-reaction step 10, and therefore represents additional feedstock for the second-stage bio-reaction step 14. Additionally, the microbe of the first bio-reaction 10 need not be killed or otherwise inactivated during the combination of the first bio-reaction product 60 and the second-stage feedstock 48, so that additional cellulase complex can continue to be produced during the bio-reaction step 14, and also provide additional single cell protein mass to the final product.

Figure 4:
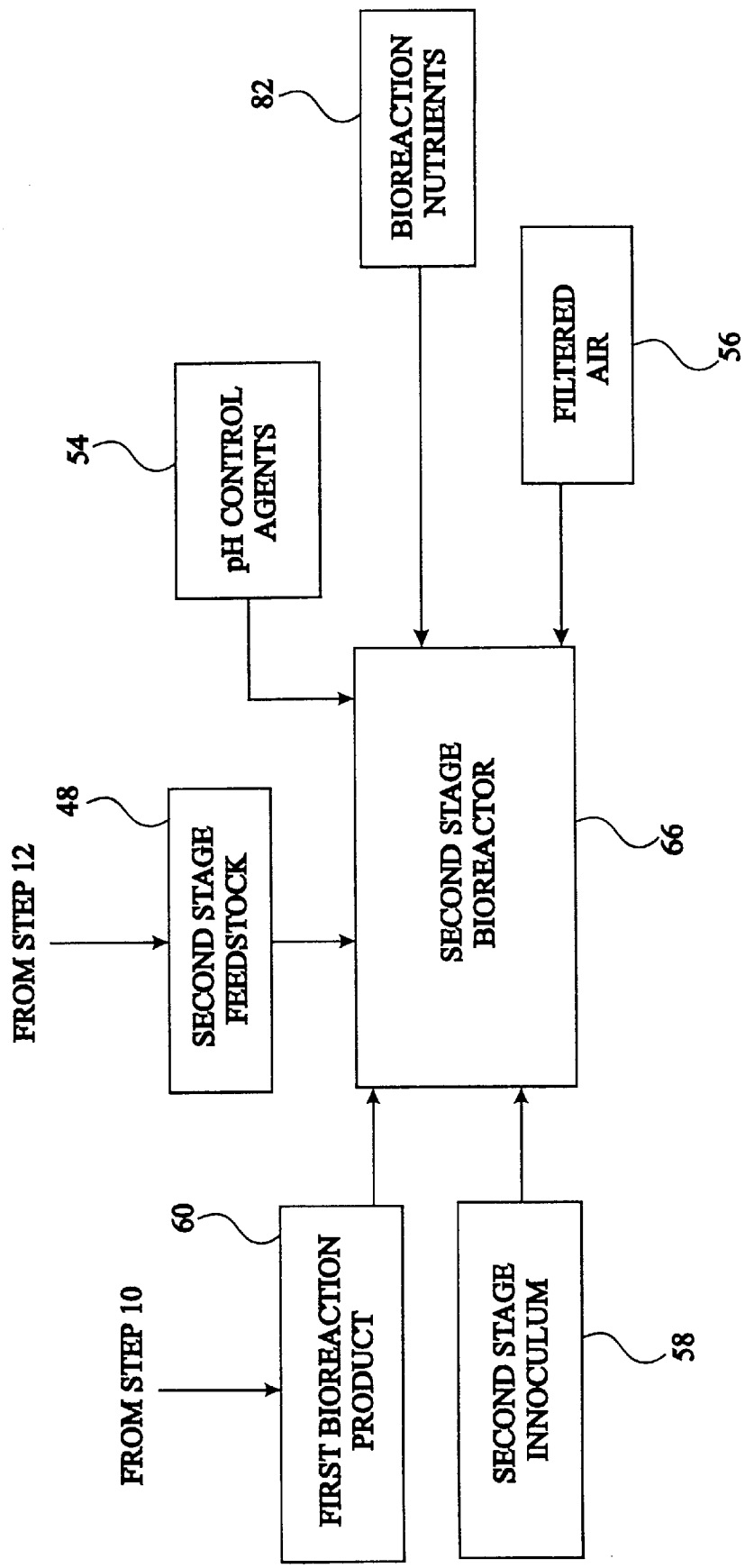
FIG. 4 is a flow diagram of the second stage bio-reaction process 14.

FIG. 4 is a flow diagram of the second-stage bio-reaction step 14. A bio-reactor 66 is of a conventional design of that of liquid bio-reactors, large enough to hold the products of the first-stage bio-reaction 10 and the second-stage feedstock pretreatment step 12. The bio-reactor 66 is temperature controlled, with controlled inputs of sterile filtered air 56, nutrients 82, and pH control agents 54. The bio-reactor 66 is initially charged with the pre-treated second-stage feedstock 48 and nutrients 82 that will initially support the second-stage bio-reaction. Bio-reaction is initiated by addition of a second stage inoculant 58, chosen in accordance with the desired product of the bio-reaction. For the production of single cell protein, it is convenient to use a microbe strain such as *Candida utilus*, while for the production of ethanol, a strain of *Saccharomyces cerevisae* can be used instead. Water can also be added as needed to provide 10–30% dry matter, or preferably, 20–25% dry matter.

After the microbes have begun vigorous growth, the first-stage bio-reaction product 60 is added to the mixture in bio-reactor 66. The amount of first-stage bio-reaction product 60 is generally small in relation to the second-stage feedstock 48, comprising just 2–3% by weight, depending upon cellulose and starch content of the second-stage feedstock. For optional cellulose utilization, 5–25 International Units of cellulase activity /g cellulose in the feedstock can be employed. When the first stage bio-reaction is inefficient, the fractional amount of bio-reaction product 60 must be higher. It is preferable for the ratio of the first bio-reaction product 60 to the second bio-reaction feedstock to be less than 10%, and even more preferable for the ratio to be less than 55%.

There can be incompatibility between the microbe used in the first-stage bio-reaction and the second-stage bio-reaction, in which case the first bio-reaction microbes would need to be killed or inactivated prior to addition of the first bio-reaction product 60, without largely affecting the enzyme activity. Such methods will be discussed in a later section.

The first bio-reaction product 60 can be treated to kill or otherwise inhibit the activity of the microbes used in the first-stage bio-reaction 10, for example by the use of ionizing radiation, such as strong ultra-violet or gamma radiation. This will prevent the growth and metabolism of the first bio-reaction microbes in the bio-reactor 66 allowing growth of the desired microbe contained within the inoculant 58. Care must be taken, however, not to destroy or inhibit the cellulase complex or other enzymes produced in the step 10, or persist so as to inhibit second-stage bio-reaction 14. In many cases, however, the presence of the microbes from the first bio-reaction 10 are not disruptive to the second bio-reaction 14. For instance, the microbe of the inoculum 20 may not grow vigorously in liquid medium, if it naturally grows on solid-medium. In addition, the microbe of the second-stage inoculant 58 is chosen generally in part for its high rates of growth in the liquid bio-reaction of step 14. Also, large amounts of biological activity in the second-stage inoculant 58 can be used so that the residual microbe from the first bio-reaction product 60 is small in comparison. Furthermore, the growth and products of the microbe from the first bio-reaction product 60 can be compatible with or equivalent to those of the microbe used for the second stage inoculant 58, so that the presence of the first-stage bio-reaction microbe in the second-stage bio-reaction is neutral to the overall process.

In one embodiment of the invention the second-stage bio-reaction can be initiated by introducing the second-stage inoculant 58 to the mixture of first-bio-reaction product 60 and second-stage feedstock 48. Filtered air 56 is introduced to maintain a proper aerobic or anaerobic environment. For example, to produce ethanol, the levels of oxygen will be highly restricted to maintain an anaerobic environment. However, for the production of single-cell protein, a highly aerobic environment will be maintained. To assist in the maintenance of an aerobic environment, the filtered air 56 can be added under pressure, maintaining a pressurized environment in the bio-reactor 66 with higher levels of dissolved oxygen in the tank. Alternatively, oxygen-streams can be added to the filtered air 56 to maintain higher oxygen levels.

During the second-stage bio-reaction, acids are frequently produced, and serve to inhibit the reaction once certain pH levels have been reached. To maintain higher pH levels, pH control agents can be added, which can include a number of base or base-producing agents as will be known and understood to those of ordinary skill in the art.

Additional bio-reaction nutrients 82 can also be added to the bio-reactor 66 from time to time in order to supplement the initial feedstock with nutrients needed for the process. These can include, but are not limited to, certain energy sources (e.g. sugar-enriched syrups), additional pre-treated feedstock 48, mineral supplements (e.g. sources of ammonium or phosphate ions, vitamins, zinc and other trace elements), and biological control agents to inhibit the growth of microbial contaminants.

The second-stage bio-reaction will frequently generate both heat and carbon dioxide. The temperature in the bio-reactor 66 must therefore be monitored and controlled, such as through the use of heat exchangers. The carbon dioxide gas produced will generally be accumulated and released in the output of the spent filtered air through the bio-reactor 66.

Agitation of the bio-reaction mixture is desirable to reduce the bubble size, thereby increasing the oxygen mass transfer from the gaseous to liquid phase. Furthermore, agitation will maintain homogeneous conditions in the presence of the solid components of the feedstock and further prevent the microbes from settling out. This agitation can involve both a physical agitation (for example from moving paddles or screws), or from the movement of the process filtered air 56 through the bio-reactor 66 or other means known in the art. Agitation should generally be maintained during the course of the bio-reaction.

Finish Process

Figure 5:
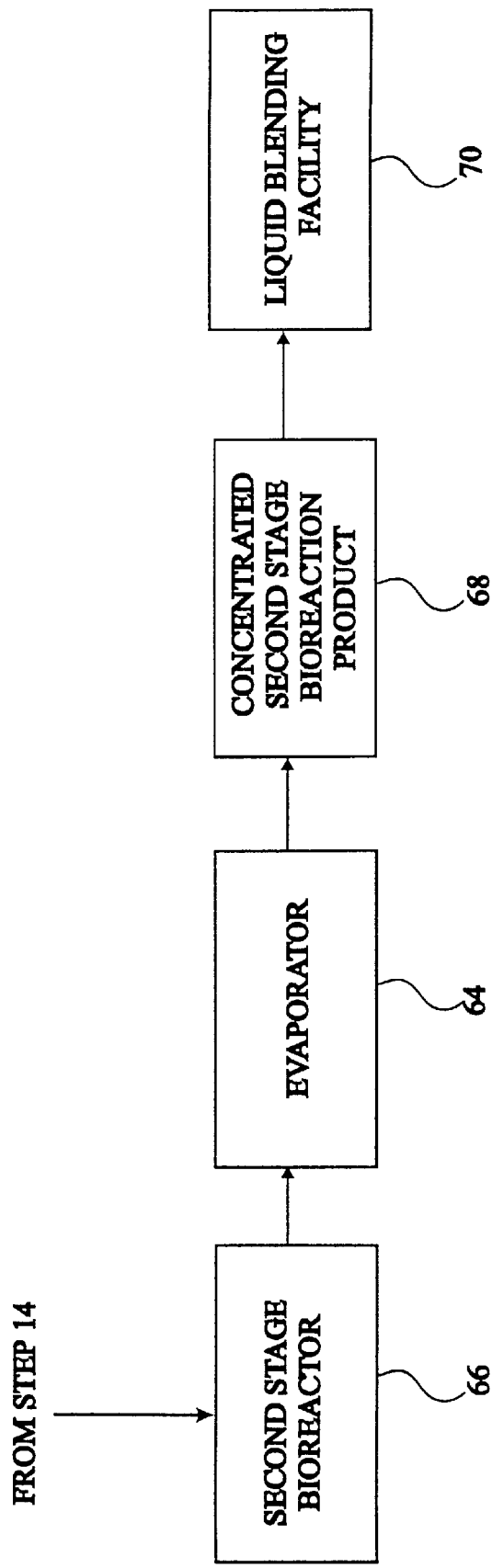
FIG. 5 is a flow diagram of the finish process 16.

Upon completion of the second-stage bio-reaction the finish process separates the desired products from the mixture contained within the bio-reactor 66, and then prepares the products for sale or further use. FIG. 5 is a flow diagram of the finish process, step 16, as would be used for the production of single cell protein product for use in animal feed.

The second-stage bio-reactor 66 will contain a relatively liquid product containing a number of different nutrients of value. The microbial biomass, representing single cell protein, is present as a suspension in the bio-reaction mixture. The mixture will also have dissolved nutrients, such as phosphate and ammonium ions, as well as low molecular weight sugars, lipids, and other biological molecules. Furthermore, the bio-reaction mixture will contain residual cellulase complex, which can serve as a feed enhancer. In addition, there will be larger contaminating particles, including cellulosic material that was incompletely hydrolyzed in the feedstock pre-treatment step 12, the first-stage product 60 that is incompletely hydrolyzed and fermented, and adhered dirt, sand, small stones and other inorganic material and contaminants from the raw second-stage feedstock.

These materials can be separated from the bio-reaction mixture, or simply be homogenized into the final product.

The homogenized mixture is passed to an evaporator 64, conveniently heated by steam, which concentrates the residual liquid single cell protein material using heat and partial vacuum to approximately 40–50% dry matter. The use of the partial vacuum allows evaporation using less heat and lower temperatures. This saves on the cost of heating the large volumes of liquor, prevents the denaturing and inactivation of residual cellulase complex in the liquor, and maintains the nutritive value of various biological agents (e.g. vitamins) present in the liquor. The evaporator 64 can also be used in the concentration and/or distillation of ethanol in cases of ethanol production.

A concentrated product 68 is produced by the evaporator 64, and can be stored awaiting further processing or sale. The product 68 is tested for the presence of different nutrients (e.g. protein, phosphate, and ammonium ion vitamins and trace elements), and is then mixed in a liquid blending facility 70 with additional nutrients to produce a more standardized product. The product of the liquid blending facility 70 is then ready for addition to animal feed as a protein supplement. Optionally a stabilizing agent to retard spoilage can be added to increase storage life.

It should be noted that the finish process 16 will be different depending on the type of product from the bio-reaction. For example, if an anaerobic fermentation is carried out in the bio-reactor 66 to produce ethanol, the ethanol would be recovered from the output vapors of the evaporator 64 as a distillate.

Utilization of High Starch Second-stage Feedstock Materials

While low-quality rural biomass and industrial waste materials are attractive economically as raw feedstock by themselves, in certain cases they can be relatively unavailable, expensive, or hard to treat or digest. The present invention can also be used, as described above, for commercial uses even using generally expensive, high-quality feedstock materials such as corn, corn meal or other cereal meals. These materials are distinguished by the high concentrations of available starch, which require amylases and other starch-hydrolyzing enzymes such as amyloglucosidase to be processed effectively.

Figure 7:
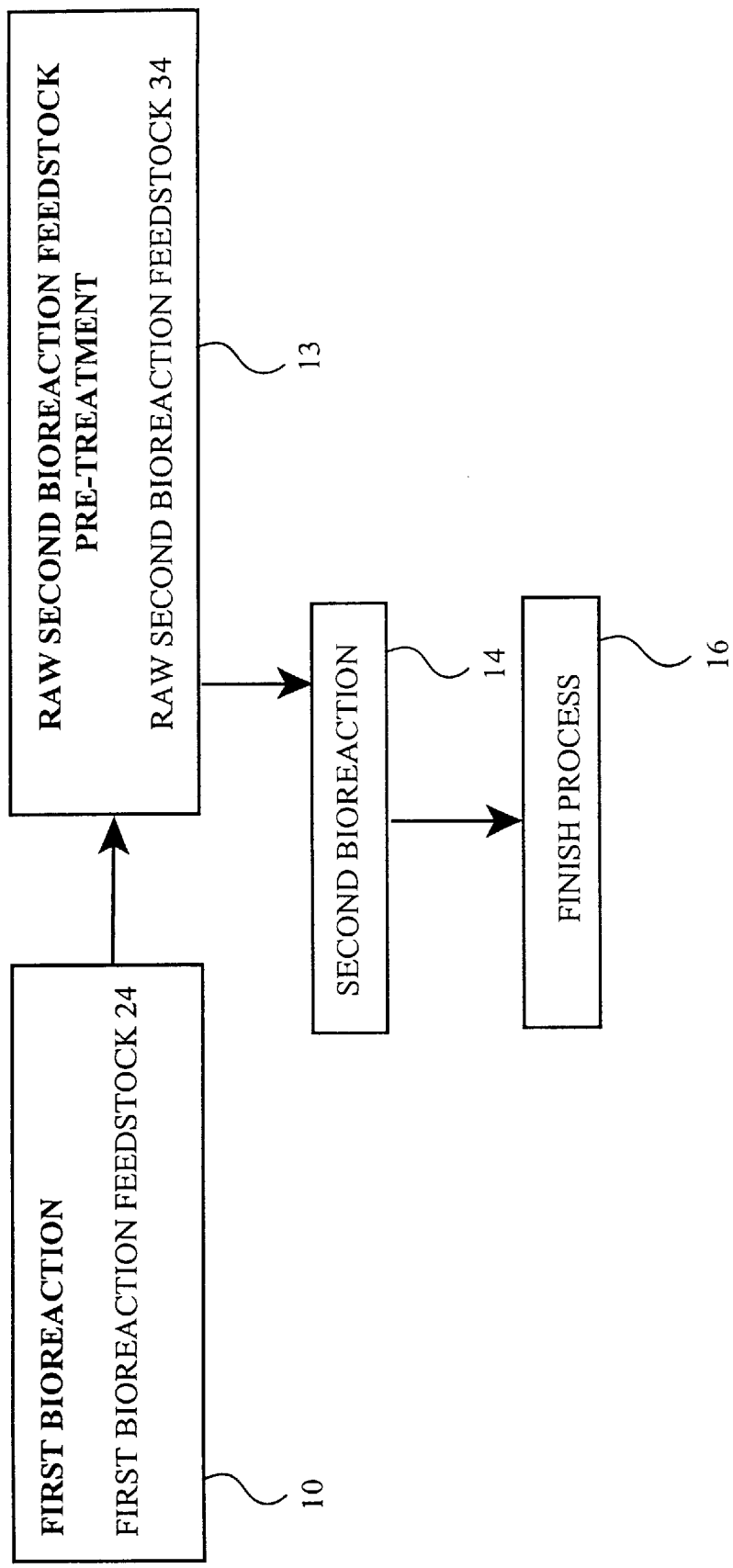
FIG. 7 is a flow diagram of first and second stage linked bio-reactions, as in FIG. 1, but with steps linked in a different order.

Processing of high-starch feedstock materials, however, presents problems when using directly the steps of processing described in FIG. 1. If a high-starch second-stage bio-reaction feedstock is pre-treated in the manner of FIG. 3, a thick, gelatinous mass is formed from the starches in the presence of heat. The extreme viscosity of the gelatinous mass prevents the neutralizing agent 50 from being evenly dispersed, and impedes the mixture of the feedstock with bio-reaction product 60. Therefore, the raw second-stage bio-reaction feedstock 34 must be treated with the first bio-reaction product 60 prior to the acid 32 hydrolysis or with heat-stable amylases that retain activity at starch-gel formation temperatures. FIG. 7 is a flow diagram showing enzyme treatment of the raw second-stage bio-reaction feedstock preceding chemical pre-treatment. This enzyme treatment reduces the high-molecular-weight starch to lower molecular weights, so that the acid hydrolysis results in a much lower viscosity mixture. Thus the order of the steps of acid and enzymatic hydrolysis of the raw second-stage feedstock are switched between the processes described in FIG. 1 and FIG. 7.

Figure 8:
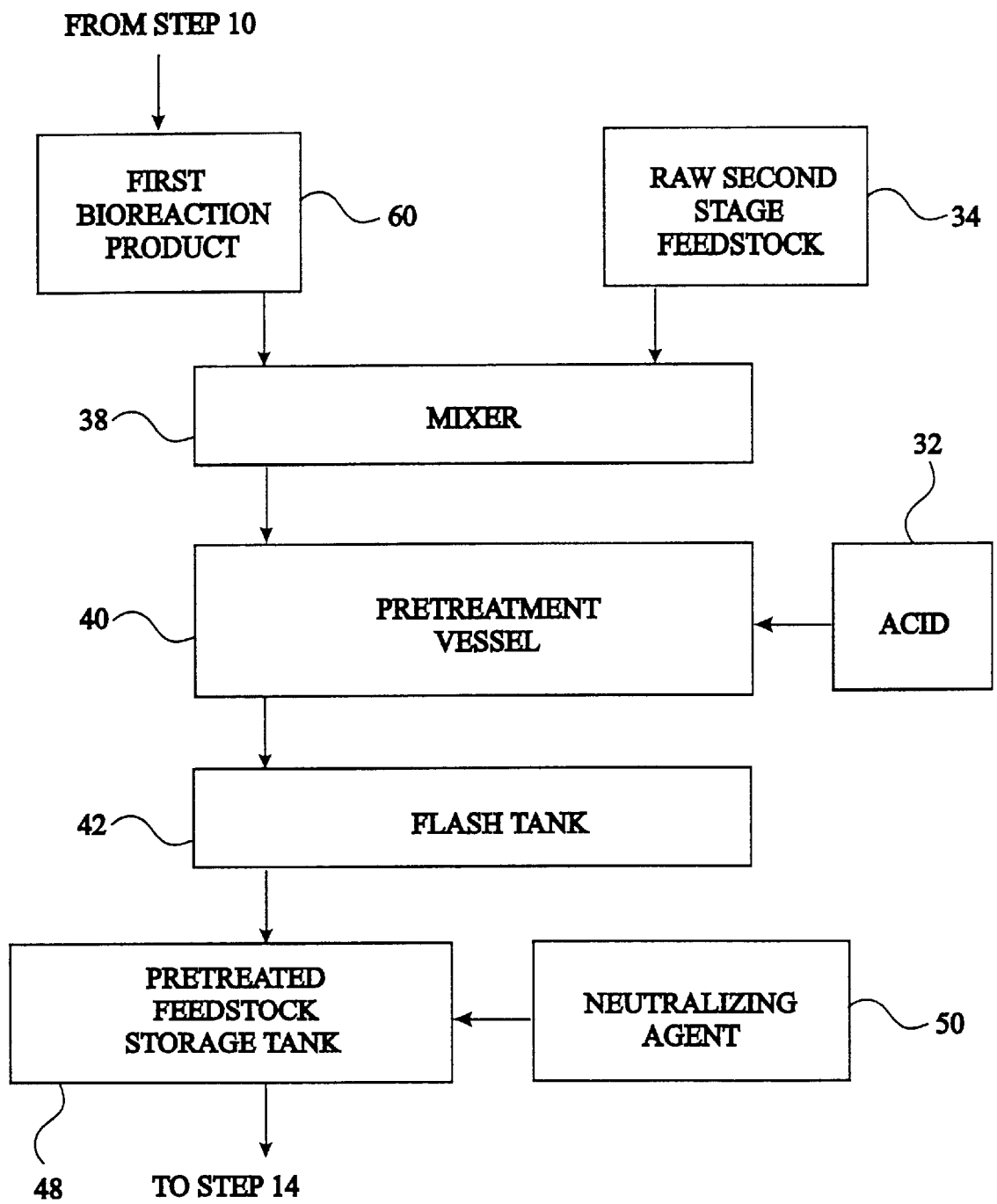
FIG. 8 is a flow diagram of the raw feedstock pre-treatment process for high-starch feedstock materials.

While the first stage bio-reaction is similar in the processes described in FIG. 1 and FIG. 7, instead of the step 12 pre-treatment process, a replacement step 13 pre-treatment process is used, shown in FIG. 8, a flow diagram. The product from step 10 is mixed in the mixer 38 with the raw second-stage feedstock 34. The resulting mixture is transferred to a pretreatment vessel, where the amylase enzyme can hydrolyze starches within the feedstock 34. It should be noted that in substitution for or addition to amylase, other enzymes can be used (e.g. endo-gluconases, proteases, or cellulases, depending on the nutriment 34). After a suitable pre-treatment, which can be as short as 30 minutes, or as long as a day, the acid 32 is added to the pre-treatment vessel and the mixture heated to further hydrolyze constituents of the mixture. The final aspects of the step 13 pre-treatment process are as described for FIG. 3.

Typical conditions for the step 13 process in small batch operation are to mix 80 gallons of water with 225 pounds of finely ground corn meal. This mixture is heated to 65° C. and add amylase enzyme sufficient for the amount of corn—e.g. 500 ml of Termamyl 120L amylase enzyme preparation (Novo Nordisk, Raleigh, N.C.). The mixture is then heated to 85° C. and incubated for 1.5 hours. Then, 6L of concentrated $H_3PO_4$ are added, and the mixture is heated to 130° C. and held for 0.5 hours. This pre-treated mixture is then pumped into a suitable pretreated feedstock storage tank 48 and held there prior to neutralization and usage in the second-stage bio-reaction. Concentrated $NH_4OH$ is added before beginning the bio-reaction in a quantity to bring the pH to 4.0–6.0, preferably 4.3 to 4.5.

The step 14 bio-reaction process is the same as that shown in FIG. 4, with the exception that the first-stage bio-reaction product 60 is not added from the step 10 as shown, but rather is supplied from the pretreated mixture storage tank 48, in this case from the step 13 rather then the step 12. It should be noted that in the case where multiple enzymes are required to break down the raw second-stage feedstock 34, it can be that elements of both FIG. 1 and FIG. 7 processes can be used. For instance, many of the starchy grains such as corn, rice, and barley, have significant cellulosic content that can be hydrolyzed for maximum efficiency—corn grain, contains about 8–9% cellulose content that is unused unless cellulase complex is added to aid in its enzymatic hydrolysis. It is convenient in such cases to hydrolyze the raw second-stage feedstock 34 with starch hydrolyzing enzymes in the manner of FIG. 7 and FIG. 8, and to then treat this mixture further with cellulose complex in the manner of FIG. 1 and FIG. 4.

When using a 15% fraction of pre-treated cracked corn as bio-reaction feed and yeast *Candida utilis* as the bio-reaction microbe, final cell density of 20 g dry cell weight per liter of bio-reaction mixture results. This yields 12 grams of protein per liter with about a 10% solid concentration.

It is also a teaching of the present invention that the product from the first-stage bio-reaction can, when properly post-treated, be a commercially important product in animal feed.

Figure 6A:
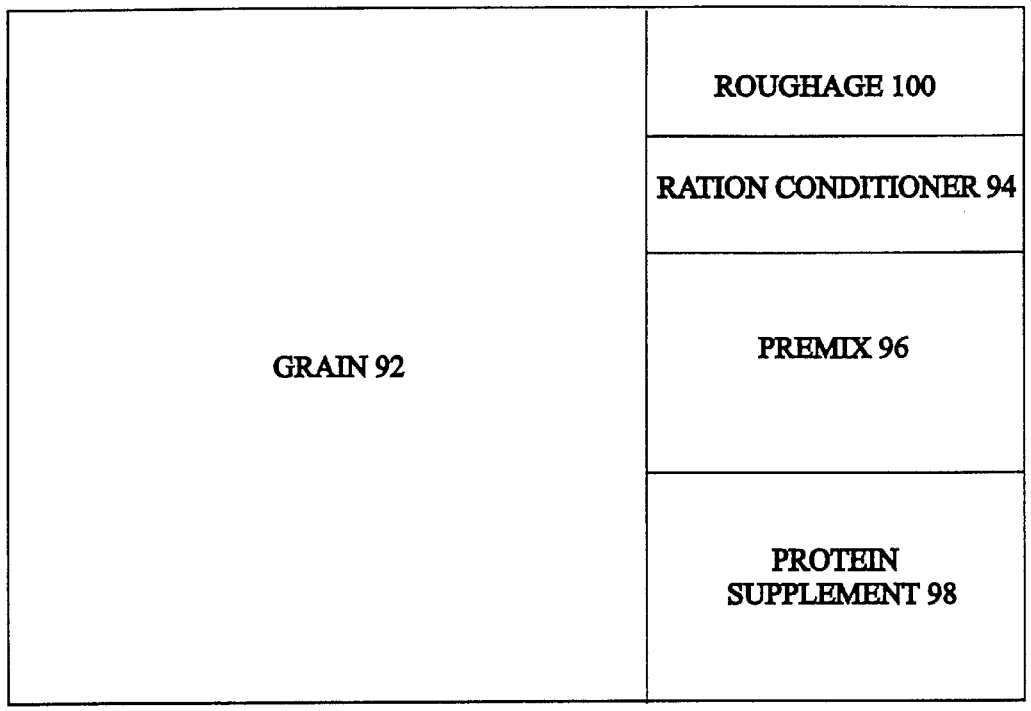
FIGS. 6A–B are schematic block diagrams depicting the constituents of standard totally mixed ration (TMR) 90 and modified TMR 102, respectively.

To understand this, consider the components of feed commonly provided to ruminants such as cattle. FIG. 6A is a schematic block diagram depicting the constituents of a Totally Mixed Ration (TMR) 90, wherein their relative proportions are roughly indicated by the relative areas corresponding to each constituent. As can be seen, grain 92, which is typically a cereal grain such as corn, is the primary constituent, and can comprise 70% or more of the TMR 90. Because the grain 92 is highly digestible, a roughage component 100 is included, in a percentage of roughly 7–12%. The roughage component 100 can include hay or some other biomass high in cellulose content.

It is well known in the art of animal feed that an optimal protein percentage in animal feed is roughly 14%, whereas the protein content of the grain 92 is typically less than 10%. Thus, additional protein sources are required. These protein supplements 98 can comprise either high-protein vegetable matter such as soybean meal, or can alternatively comprise chemical additives such as urea or ammonium chloride, which provide nitrogen sources that can be used by the feeding animals to make protein. It should be noted that the single-cell protein product the step 16 of FIG. 5 can be used as the protein supplement 98 in animal feed. The protein supplement 98 can comprise as much as 10% or more of the TMR 90.

In addition, a pre-mix 96 is commonly provided that contains vitamins, minerals, amino acids, drugs and other additives that improve animal health and growth. These additives can include enzymes that aid in the digestion of the other TMR 90 constituents, most importantly the grain 92. This premix commonly comprises less than 10% of the mass of the TMR 90.

A ration conditioner 94 is a liquid used to bind together the constituents described above (the grain 92, the roughage 100, the premix 96 and the protein supplement 98), since these other constituents are generally dry or of low enough liquid content that the many constituents are not bound together. The ration conditioner 94 is often comprised of molasses and bitter waste products of sugar production, as well as fatty materials.

Figure 6B:
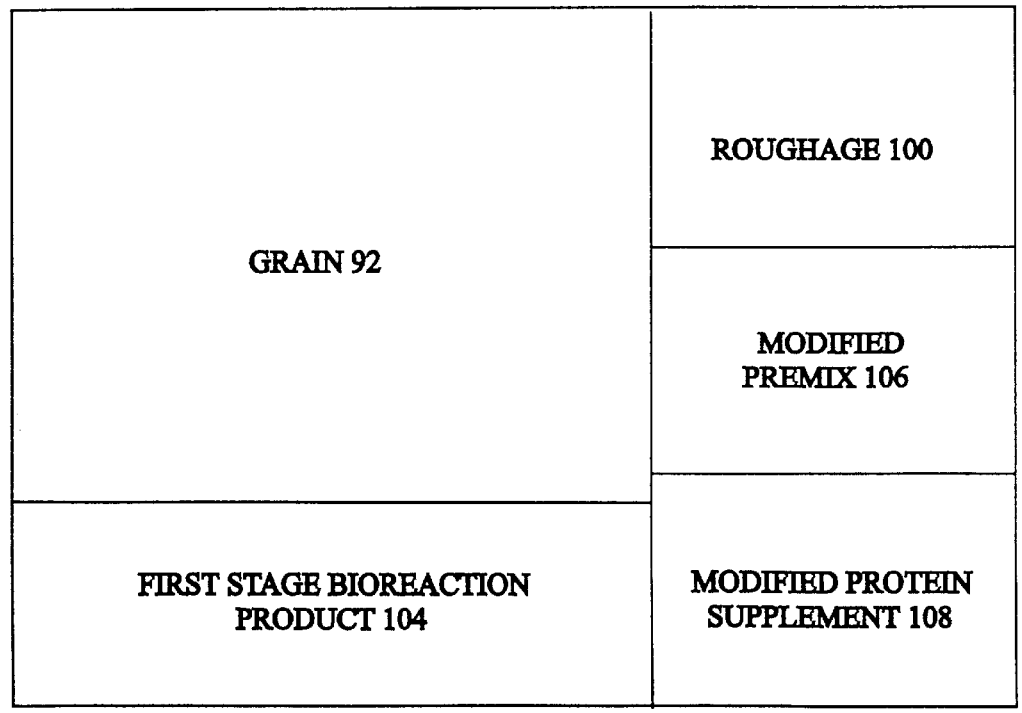

FIG. 6B is a schematic block diagram depicting the constituents of a modified Totally Mixed Ration (TMR) 102 according to the present invention, wherein their relative proportions are roughly indicated by the relative areas corresponding to each constituent. It can be seen that the major constituent is still the cereal grain 92, such as corn, and that roughage 100 is still required. However, the fraction of the grain 92 relative to the total modified TMR 102 is reduced, since the nutritive elements (e.g. carbohydrates, fat, and protein) originally supplied by the grain 92 in the TMR 90 is now partially replaced by a first-stage bio-reaction product 104. The fraction of product 104 relative to the grain 92 varies according to the type of grain 92 and the product 104. In general, should the product 104 have few beneficial nutrients, but be used primarily for its enzyme content, then the smallest amount of product 104 that provides sufficient enzymatic activity will be used. This will generally be in the range of 5–10% weight fraction of the grain 92. However, if the product has nutritional value in addition to its enzyme content, it may be added in much larger fractional quantity. For example, amylase-enhanced SBG contains significant carbohydrate, mineral, and even protein content, and yet is less expensive to produce than the grain 92 it is replacing. Thus, it can be advantageous to replace as much as 40% or more of the grain 92 with such amylase-enhanced SBG.

The bio-reaction product 104 is very similar to the first-stage bio-reaction product 60.

The product 104, however, is treated as described below so as to reduce degradation of the enzyme produced, as well as to diminish putrefaction that might result from prolonged storage at ambient or near ambient temperatures. Depending on factors known to those of skill in the art of animal feed formulation, the microbes that are grown in first-stage bio-reaction can be killed during the treatment or the viability of these microbes can be maintained. Embodiments of these alternatives will be described below.

The presence of the bio-reaction product 104 has many benefits in animal feed. Firstly, the enzymes that are made during the bio-reaction are generally selected so as to have hydrolyzing activity against the grain 92 components, as well as a modified protein supplement 108. By hydrolyzing these components, the nutritive value of the component is made more available to the animal feeding on the modified TMR 102. Secondly, the enzymes can retain their activity after ingestion by the animal, thus continuing to hydrolyze food stuffs after they have been physically macerated by the animal and chemically acted upon by chemicals and additional enzymes from and in the animal's digestive tract. Thirdly, the bio-reaction microbes, if still alive, can produce additional hydrolyzing enzymes with benefits as outlined above, as well as serve through their constituents, such as proteins, nucleic acids, fats, and carbohydrates, as a nutritive source for the animal.

Because the product 104 can contain additives used to encourage the growth of the enzyme-production microbes, such additives possibly to include non-protein nitrogen sources such as urea or ammonium salts, and additionally because the microbes can serve as protein sources, the protein supplement 98 can be altered to be the modified protein supplement 108. This modified protein supplement 108 can contain either smaller amounts of non-protein nitrogen sources, less high-protein vegetable matter. or both.

For similar reasons, the premix 96 can be modified to become a modified premix 106, perhaps containing fewer minerals and vitamins, according to their presence in the product 104. The enzymes which can be provided in the premix 96 are reduced or eliminated if they are already present in the product 104.

Because the product 104 generally has considerable water content, even if the bio-reaction is performed as a solid substrate bio-reaction, the product 104 can serve as a partial or total substitute for the ration conditioner 94 by binding the other modified TMR 102 components.

Thus, the product 104 can serve the functionality, in total or in part, of some of the constituents of standard Totally Mixed Ration 90. Furthermore, because of the high concentration of enzyme which aids in the digestion of the vegetable-derived nutrition, the efficiency of digestion of the modified TMR 102 is higher than that of the standard TMR 90. Furthermore, because the first-stage feedstock 24 is generally derived from an inexpensive biomass or food production waste, such as spent brewers grain (SBG), the overall cost of production of the modified TMR 102 is less than that of the standard TMR 90. With both higher digestive efficiency, as well as lower cost of production, the commercial importance of the modified TMR 102 is apparent.

The Totally Mixed Ration 90 in the composition described above, is of particular use for ruminant animals. However, mono-gastric organisms (e.g. swine and poultry) have somewhat different requirements to complement the particular needs of the feeding animal. For example, poultry feed generally does not have added roughage, but care must be taken to prevent β-glycan presence in food, since β-glycan can cause blockage in the poultry gastrointestinal tract. Feeding poultry product 104 with bio-reaction-produced β-glycanase will prevent such problems, and allow a wider range of grain 90 and other constituents to be added to such feed.

Similarly, fish grown in aquaculture are provided high-protein diets, in order to provide rapid animal growth. However, when fed proteins in high concentration, fish tend to suffer from digestion problems. The presence of proteases in product 104 will reduce these problems.

Process Results

In an anaerobic process example, corn stover was used as the raw second-stage bio-reaction feedstock, and was pretreated with 0.05M phosphoric acid at 160° C. for 20 minutes. Cellulase-complex enzymes at 1 part dry weight enzyme/fungus mixture to 9 parts pre-treated corn stover dry weight were combined, and were inoculated with 1 part in 20 of 5% (w/v) of yeast *S. cerevisiae* and incubated anaerobically for 48 hours. About 175 mg of ethanol per gram of corn stover dry mass was produced, and significantly, over 100 mg of cellibiose per gram of dry mass was also produced. Since *S. cerevisiae* cannot utilize cellibiose, whereas other microbes can, the presence of cellibiose suggests that the use of another microbe can yield even higher amounts of ethanol.

What is claimed is:

1. A process for producing an animal feed supplement comprising the steps of:
    (a) providing a first-stage bio-reaction feedstock in a solid substrate bio-reaction mixture containing microbial growth nutrients, in a bioreactor;
    (b) inoculating the first-stage feedstock with a culture of a microorganism capable of secreting degradative enzymes wherein said microorganism is selected from the group consisting of *Trichoderma reesei, Trichoderma hamatum*, Gliocladium, *Aspergillus oryzae, Aspergillus niger, Rhizopus oligosporus, Rhizopus oryzae, Clostridium thermocellum, Phanerochaete chrysoporium* or mixtures thereof, thereby producing a first bio-reaction mixture;
    (c) incubating the first bio-reaction mixture for a time and under conditions sufficient to produce a first-stage bio-reaction product;
    (d) pretreating a raw second-stage bio-reaction feedstock by contacting the raw second-stage feedstock with phosphoric acid for a time sufficient to hydrolyze hemicellulose, to produce free lignin, and cellulose in the second-stage feedstock, then;
    (e) neutralizing the acid, whereby a second-stage bio-reaction feedstock is prepared;
    (f) combining the second-stage bio-reaction feedstock with the product of the first-stage bio-reaction of step (c) and a second-stage bio-reaction microorganism of Saccharomyces or Candida, whereby the second-stage bio-reaction is initiated;
    (g) incubating the second-stage bio-reaction for a time and under conditions sufficient to produce an animal feed supplement; and
    (h) recovering an animal feed supplement.

2. The process of claim 1 wherein the phosphoric acid is neutralized with a nitrogen-containing base.

3. The process of claim 1 further comprising the step of inactivating microorganisms of the first stage bio-reaction product without inactivating the enzyme activity in said first stage bio-reaction product.

4. The process of claim 1 wherein more than 30% of the dry matter of the second stage bio-reaction feedstock is cellulose.

5. The process of claim 1 wherein the second-stage bio-reaction microorganism is *Saccharomyces cerevisiae* or *Candida utilis*.

6. The process of claim 1 wherein the first-stage bio-reaction feedstock is spent brewer's grain.

7. The process of claim 1, wherein the first bio-reaction feedstock comprises cereal grain.

8. The process of claim 1, wherein the solid substrate bio-reaction mixture has less than 40% dry mass content.

* * * * *